United States Patent [19]
Wasserman et al.

[11] Patent Number: 4,536,510
[45] Date of Patent: Aug. 20, 1985

[54] METHOD OF ANTAGONIZING THE EFFECTS OF THROMBOXANE

[75] Inventors: Martin A. Wasserman, Ambler, Pa.; Barry M. Weichman, Voorhees, N.J.

[73] Assignee: Smith Kline Beckman Corporation, Philadelphia, Pa.

[21] Appl. No.: 516,221

[22] Filed: Jul. 22, 1983

[51] Int. Cl.³ .............................................. A61K 31/47
[52] U.S. Cl. ..................................................... 514/308
[58] Field of Search ......................................... 424/258

[56] References Cited

U.S. PATENT DOCUMENTS 4,243,671  1/1981  Harris et al. ..................... 424/273 R
4,315,935  2/1982  Ali ..................................... 424/258

OTHER PUBLICATIONS

The Pharmacologist, vol. 25, No. 3, 1983, p. 122, #116; Inhibition of Thromboxan-Induced Bronchoconstriction by SK&F 88046 in Anesthetized Dogs; Malo et al. The Pharmacologist, vol. 25, No. 3, 1983, p. 122, #117; SK&F 88046; A Functional Antagonist of In Vitro Bronchoconstriction Induced by Arachidonate Products; Wasserman et al.

Primary Examiner—Leonard Schenkman
Assistant Examiner—Joseph A. Lipovsky
Attorney, Agent, or Firm—Richard D. Foggio; Alan D. Lourie

[57] ABSTRACT

Methods of antagonizing the effects of thromboxane $A_2$ in the circulatory system of an animal which comprises administering to said animal a nontoxic effective amount of N,N'-bis[7-(3-chlorobenzeneaminosulfonyl)-1,2,3,4-tetrahydroisoquinolyl]disulfonylimide or a pharmaceutical acceptable salt thereof are valuable in the treatment of diseases in which thromboxane $A_2$ is a factor, such as thrombosis, endotoxic shock and cardiac anaphylaxis.

8 Claims, No Drawings

METHOD OF ANTAGONIZING THE EFFECTS OF THROMBOXANE

BACKGROUND OF THE INVENTION

Thromboxane $A_2$ ($TxA_2$), which is a product of the "arachidonic acid cascade", has been found to be a very potent platelet aggregator and pulmonary and systemic vasoconstrictive agent. $TxA_2$ is produced by the conversion by thromboxane synthetase of the prostaglandin endoperoxide, and $PGH_2$, which is a cyclooxygenase metabolite of arachidonic acid. $TxA_2$ has been suggested as an important mediator of thrombosis, endotoxic shock, pulmonary hypertension and cardiac anaphylaxis. By antagonizing the effects of $TxA_2$ in the circulatory system the compound of this invention is valuable in the treatment of diseases in which $TxA_2$ is a factor.

N,N'-Bis[7-(3-chlorobenzeneaminosulfonyl)-1,2,3,4-tetrahydroisoquinolyl]disulfonylimide, which is disclosed and claimed in U.S. Pat. No. 4,315,935 as antagonizing the effects of slow reacting substance of anaphylaxis (SRS-A) on bronchial smooth muscle, has been discovered to be an end organ antagonist of $TxA_2$. Therefore, it would be useful in the treatment of diseases in which $TxA_2$ is a factor.

DETAILED DESCRIPTION OF THE INVENTION

The present invention relates to (1) a method of antagonizing the effects of thromboxane $A_2$ ($TxA_2$) in the circulatory system of an animal and (2) a method of inhibiting platelet aggregation in an animal which comprises administering to said animal a nontoxic effective amount of N,N'-bis[7-(3-chlorobenzeneaminosulfonyl)-1,2,3,4-tetrahydroisoquinolyl]disulfonylimide or a pharmaceutically acceptable salt thereof.

The $TxA_2$ antagonist activity of N,N-bis[7-(3-chlorobenzeneaminosulfonyl)-1,2,3,4-tetrahydroisoquinolyl]disulfonylimide has been demonstrated both in vitro and in vivo. The test systems employed included: (a) antagonism of the contractions of isolated tracheal and lung parenchymal strips elicited by a stable thromboxane analog; (b) prevention of human platelet aggregation dependent on thromboxane and (c) antagonism of the bronchospasm elicited by a thromboxane mimic in vivo. The protocols and results of these test systems are shown below.

Antagonism of Contractions Elicited by Carbocyclic Thromboxane $A_2$ ($CTA_2$), a Synthetic Thromboxane Mimic Isolated guinea pig tracheas or paired lung parenchymal strips were attached via silk suture to force displacement transducers for recording changes in isometric tension. The tissues were equilibrated for one hour in modified Krebs' buffer at 37.5° C. and aerated with 95% $O_2$/5% $CO_2$. Then, the tissues were equilibrated for 30 additional minutes with N,N'-bis[7-(3-chlorobenzeneaminosulfonyl)-1,2,3,4-tetrahydroisoquinolyl]disulfonylimide (Compound I) ($1 \times 10^{-5} M$) or buffer. Contraction of the tissues was then elicited by increasing the bath concentration of $CTA_2$ in a cumulative fashion. The contractile responses were recorded as changes in mg tension.

RESULTS:

| Tissue | $CTA_2$ Concentration (M) | Control (mg tension) | (+) Compound I (mg tension) |
| --- | --- | --- | --- |
| Lung parenchyma | $10^{-8}$ | 45.5 ± 11.4 (10) | 0 (10) |
| | $10^{-7}$ | 103.5 ± 23.7 (10) | 0 (10) |
| | $10^{-6}$ | 181.5 ± 23.3 (10) | 0 (10) |
| Trachea | $10^{-8}$ | 0 (7) | 0 (7) |
| | $10^{-7}$ | 125.0 ± 33.5 (7) | 0 (7) |
| | $10^{-6}$ | 360.0 ± 89.8 (7) | 42.9 ± 20.2 (7) |

Note:
Each tissue receiving Compound I responded normally to challenge with reference contractile agonists: $1 \times 10^{-3}$ M histamine on the lung parenchyma and $1 \times 10^{-5}$ M carbachol on the trachea. The number in parentheses refers to the number of tissues studied.

Inhibition of Human Platelet Aggregation

Platelet-rich plasma (PRP) and platelet-poor plasma (PPP) are prepared from citrated blood of drug-free human volunteers and are stored at room temperature for at least 30 minutes before use. Each PRP sample is preincubated two minutes at 37° C. prior to addition of N,N-bis[7-(3-chlorobenzeneaminosulfonyl)-1,2,3,4-tetrahydroisoquinolyl]disulfonylimide (Compound I) or agonists; Compound I is preincubated for 1 minute prior to addition of agonist. A dose response is determined for each agonist, and a concentration which gives a biphasic response is selected. Compounds are tested for inhibition of the response (control response) generated by this agonist concentration. A time is selected, and the height at which the various curves intersect this time line is measured and expressed in mm (a measure of light transmittance). The difference between the response of the control and that with inhibitor present is used to calculate percent inhibition. This value is plotted against inhibitor concentrations to determine the $IC_{50}$ (the inhibitory concentration of Compound I which inhibits aggregation by 50%).

Compound I inhibits both the primary and secondary wave of platelet aggregation induced by: collagen, arachidonic acid and U-44069, a structural prostaglandin endoperoxide analog, yet functional thromboxane $A_2$ mimic. It also inhibits secondary aggregation induced by platelet activating factor and the calcium ionophore, A23187. The $IC_{50}$ for all these agonists are as follows:

| Agonist | $IC_{50}$ ($\mu M$) |
| --- | --- |
| Inhibition of Primary Phase | |
| Arachidonic acid | 19 |
| Collagen | 10 |
| U-44069 | 2.5 |
| Inhibition of Secondary Phase | |
| U-44069 | 1.7 |
| A23187 | 12 |
| Platelet Activating Factor (PAF) | 4.5 |

Protection in a Drug-Induced Canine Bronchospasm

N,N-Bis[7-(3-chlorobenzeneaminosulfonyl)-1,2,3,4-tetrahydroisoquinolyl]disulfonylimide (Compound I) had a protective effect in canine bronchoconstriction induced by U-44069. Bronchopulmonary responses to these agents were measured by computer analyses in 5 spontaneously breathing, anesthetized mongrel dogs. In a dose range of 0.3–3.0 $\mu g/kg$ i.v., the endoperoxide analog produced dose-related alterations in pulmonary airway resistance, dynamic lung compliance, expiratory airflow rate, tidal volume and respiratory frequency. Pretreatment with Compound I (5.0 mg/kg i.v.) produced an inhibition of the bronchospasm with a characteristic shift to the right of the control U-44069 curve. Inhibition by Compound I occurred in all pulmonary parameters calculated.

| Drug | U-44069 Dose ($\mu$g/kg i.v.) | Increase in resistance to movement of air into the lungs (%) | Decrease in ability of lungs to expand easily (%) |
| --- | --- | --- | --- |
| resting baseline | | 0 | 0 |
| U-44069 | 0.3 | 67 | 28 |
| | 1.0 | 333 | 56 |
| | 3.0 | 549 | 70 |
| pretreat with Compound I (5 mg/kg), then repeat U-44069 | 0.3 | 14 | 5 |
| | 1.0 | 30 | 13 |
| | 3.0 | 56 | 28 |

It is clear from the above data that N,N'-bis[7-(3-chlorobenzeneaminosulfonyl)-1,2,3,4-tetrahydroisoquinolyl]disulfonylimide antagonizes the effect of thromboxane $A_2$ and inhibits the aggregation of platelets.

The methods in accordance with the instant invention comprises administering to an animal in need of: (1) antagonism of the effects of thromboxane $A_2$; or (2) the inhibition of platelet aggregation the compound N,N'-bis[7-(3-chlorobenzeneaminosulfonyl)-1,2,3,4-tetrahydroisoquinolyl]disulfonylimide or a pharmaceutically acceptable salt thereof, usually combined with a pharmaceutical carrier, in a nontoxic effective amount of about 50 to about 500 mg of the compound. The route of administration is preferably parenteral. For parenteral administration the pharmaceutical composition will be in the form of a sterile injectable liquid such as an ampul or an aqueous or nonaqueous liquid suspension. For convenience equal doses will be administered 1 to 4 times daily with the daily dosage regimen being selected from about 50 to 2000 mg.

The pharmaceutical preparations are made following the conventional techniques of the pharmaceutical chemist as appropriate to the desired end product. The following example illustrates the preparation of such a composition used in the method of the instant invention.

N,N'-Bis[7-(3-chlorobenzeneaminosulfonyl)-1,2,3,4-tetrahydroisoquinolyl]disulfonylimide is dissolved in sterile water at a concentration of 0.5 percent and placed in an sterile ampul for parenteral administration.

What is claimed is:

1. A method of antagonizing the effects of thromboxane $A_2$ in the circulatory system of an animal which comprises administering to an animal in need of said antagonism a nontoxic effective amount of the active ingredient, N,N'-bis[7-(3-chlorobenzeneaminosulfonyl)-1,2,3,4-tetrahydroisoquinolyl]disulfonylimide or a pharmaceutically acceptable salt thereof.

2. A method of claim 1 in which a daily dosage of from about 50 to about 2000 mg of active ingredient is administered.

3. A method of claim 1 in which the active ingredient is administered with a pharmaceutical carrier.

4. A method of claim 3 in which the administration is parenteral.

5. A method of inhibiting platelet aggregation which comprises administering to a subject in need of said inhibition a nontoxic effective amount of the active ingredient, N,N'-bis[7(3-chlorobenzeneaminosulfonyl)-1,2,3,4-tetrahydroisoquinolyl]disulfonylimide or a pharmaceutically acceptable salt thereof.

6. A method of claim 5 in which a daily dosage of from about 50 to about 2000 mg of active ingredient is administered.

7. A method of claim 5 in which the active ingredient is administered with a pharmaceutical carrier.

8. A method of claim 7 in which the administration is parenteral.

* * * * *